United States Patent
Morsi

(10) Patent No.: US 7,914,549 B2
(45) Date of Patent: Mar. 29, 2011

(54) MECHANICAL EMBOLECTOMY AND SUCTION CATHETER

(76) Inventor: Hesham Morsi, Houston, TX (US)

(*) Notice: Subject to any disclaimer, the term of this patent is extended or adjusted under 35 U.S.C. 154(b) by 560 days.

(21) Appl. No.: 11/620,387

(22) Filed: Jan. 5, 2007

(65) Prior Publication Data

US 2008/0167678 A1    Jul. 10, 2008

(51) Int. Cl.
*A61M 29/00* (2006.01)

(52) U.S. Cl. .......................................... 606/200

(58) Field of Classification Search .............. 606/110, 606/113, 114, 127, 128, 158, 159, 194, 192, 606/200; 604/101.01, 101.05, 101.03, 509
See application file for complete search history.

(56) References Cited

U.S. PATENT DOCUMENTS

| | | | | |
|---|---|---|---|---|
| 4,141,364 | A * | 2/1979 | Schultze | 128/207.15 |
| 4,762,130 | A * | 8/1988 | Fogarty et al. | 606/159 |
| 5,112,347 | A | 5/1992 | Taheri | |
| 5,129,910 | A * | 7/1992 | Phan et al. | 606/127 |
| 5,135,484 | A * | 8/1992 | Wright | 604/28 |
| 5,192,290 | A | 3/1993 | Hilal | |
| 5,395,333 | A * | 3/1995 | Brill | 604/101.05 |
| 5,439,445 | A * | 8/1995 | Kontos | 604/103.1 |
| 5,456,666 | A * | 10/1995 | Campbell et al. | 604/103.08 |
| 5,769,871 | A | 6/1998 | Kelly | |
| 6,148,222 | A * | 11/2000 | Ramsey, III | 600/380 |
| 6,254,571 | B1 * | 7/2001 | Hart | 604/107 |
| 2001/0012951 | A1 * | 8/2001 | Bates et al. | 606/200 |
| 2002/0049408 | A1 * | 4/2002 | Van Moorlegem et al. | 604/101.01 |
| 2002/0049452 | A1 * | 4/2002 | Kurz et al. | 606/127 |
| 2002/0147458 | A1 * | 10/2002 | Hiblar et al. | 606/159 |

FOREIGN PATENT DOCUMENTS

JP    06030943    2/1994

OTHER PUBLICATIONS

English Abstract of JP 06030943.
International Search Report and Written Opinion for PCT/US2008/050235 dated Apr. 24, 2008 (13 pages).

* cited by examiner

*Primary Examiner* — Anhtuan T Nguyen
*Assistant Examiner* — David Eastwood
(74) *Attorney, Agent, or Firm* — David McEwing

(57) ABSTRACT

A novel catheter and methods for using the same are described herein. Embodiments of the catheter utilize sets of expandable members which collapse into recesses which are part of the catheter body. The recesses provide the catheter body with a low profile for insertion of the catheter into small blood vessels. In addition, the recesses may comprise openings for capturing emboli and clots by suction.

26 Claims, 5 Drawing Sheets

MECHANICAL EMBOLECTOMY AND SUCTION CATHETER

CROSS-REFERENCE TO RELATED APPLICATIONS

Not applicable

STATEMENT REGARDING FEDERALLY SPONSORED RESEARCH OR DEVELOPMENT

Not applicable.

FIELD OF THE INVENTION

Embodiments of the invention relates generally to catheters and more particularly, to catheters for use as embolectomy catheters and angioplasty catheters for treating diseases including but not limited to stroke. Still more particularly, embodiments of the invention relates to the use of balloon or expanding catheters for the treatment and/or removal of emboli.

BACKGROUND

Expanding catheters are commonly used in surgical procedures to remove emboli or blood clots from an occluded branch or vessel. An embolus is most frequently a blood clot, but it can also be plaque broken off from an atherosclerotic blood vessel or a number of other substances including fat, air, and even cancerous cells. Typically, the catheter is inserted percutaneously to the vicinity of the clot and expanded, capturing a portion of the clot, which is then withdrawn from the vessel upon removal of the catheter. One mechanism for expansion of a catheter is inflation.

Catheters with inflatable balloon means have been provided for blood clot removal. U.S. Pat. No. 4,762,130 to Fogarty discloses such a catheter. The Fogarty device uses a single, spiral-configured balloon U.S. Pat. No. 6,254,571 to Hart discloses a second type of catheter for removing occlusive materials from body passages, in which a plurality of mechanically activated expandable segments are disposed on the distal end of a catheter.

Embolectomy catheters have also been provided with balloons having small flexible protrusions adapted to bite into the clot upon inflation of the balloons, enabling a portion of the clot to be pulled free by withdrawal of the catheter. Such a catheter is shown in U.S. Pat. No. 3,635,223 to Klieman. Various other means for removing emboli exist, including coil-shaped and basket-shaped devices, which typically are constructed of wire or the like. None of these are consistently effective for clot removal, largely because new clots tend to be less organized and therefore more delicate.

Existing expandable catheters may suffer from several other problems. For example, if such a catheter comprises a single balloon and it is inflated near a well-organized clot, expansion of the balloon may result in the application of excessive force to the delicate vessel wall. Second, if a single expanded balloon catches the clot and the clot is large, the process of removing the clot may also create excessive forces on the vessel. Such procedures may damage the wall of the vessel. Expanding catheters that do not engage most of the clot mass may not trap and retain a large portion of the clot, especially upon withdrawal of the catheter from the vessel. Furthermore, present catheters do not present a low enough profile for easy insertion into extremely small diameter vessels such as those found in the brain.

Accordingly, there remains a need in the art for an angioplasty or embolectomy catheter that can capture, retain, and remove all or a significant portion of the blood clot without producing excessive pressure on the vessel. In addition, there is a need in the art for devices that can be inserted into extremely small diameter vessels.

SUMMARY OF SOME OF THE PREFERRED EMBODIMENTS

A novel catheter and methods for using the same are described herein. Embodiments of the catheter utilize sets of expandable members which collapse into recesses which are part of the catheter body. The recesses provide the catheter body with a low profile for insertion of the catheter into small blood vessels. In addition, the recesses may comprise openings for capturing emboli and clots by suction. Further features and advantages of the catheter will be disclosed below, but preferably the invention is not so limited and includes variations to such embodiments as recognized by this skilled in the art.

In an embodiment, a catheter comprises a catheter body having an inner lumen, an outer lumen, and one or more recesses disposed along said catheter body. Each recess includes at least one opening to said inner lumen. The inner lumen and outer lumen are sealed from each other. The catheter further comprises one or more expandable members disposed along said catheter body in fluid communication with said outer lumen. Each expandable member has an expanded position and a contracted position. Moreover, each expandable member in said contracted position fits within one of said plurality of recesses.

In an additional embodiment, a device for removal of an embolus from a vessel comprises a guiding catheter. The device further comprises a catheter slidably disposed within said guiding catheter. The catheter has an inner lumen, a plurality of radially expandable members disposed axially along said catheter, and a plurality of recesses. Each recess corresponds to one of said plurality of expandable members, and each recess has at least one opening in fluid communication with said inner lumen.

In another embodiment, method of removing at least a portion of an embolus from a vessel comprises providing a catheter comprising an inner lumen, an outer lumen, a plurality of radially expandable members in fluid communication with the outer lumen, and a plurality of recesses disposed along said catheter. Each recess includes at least one opening to said inner lumen. The method also comprises inserting the catheter into an occluded vessel. The plurality of members are in a contracted position within the plurality of recesses. In addition, the method comprises engaging an embolus between said members by expanding said plurality of members. Moreover, the method comprises capturing at least a portion of said embolus in said plurality of recesses by contracting said plurality of members. The method further comprises removing the embolus by withdrawing said catheter from the vessel.

In an embodiment, the method also comprises applying vacuum through the at least one opening in each recess from the inner lumen to capture at least a portion of the embolus.

Thus, embodiments described herein comprise a combination of features and advantages intended to address various shortcomings associated with certain prior devices. The various characteristics described above, as well as other features, will be readily apparent to those skilled in the art upon reading the following detailed description of the embodiments, and by referring to the accompanying drawings. It should be appreciated by those skilled in the art that the conception and the embodiments disclosed may be readily utilized as a basis for modifying or designing other structures for carrying out the same purposes of the embodiments described herein. It should also be realized by those skilled in the art that such equivalent constructions do not depart from the spirit and scope of the invention as set forth in the appended claims.

BRIEF DESCRIPTION OF THE DRAWINGS

For a detailed description of embodiments of the invention, reference will now be made to the accompanying drawings in which.

Figure 1:
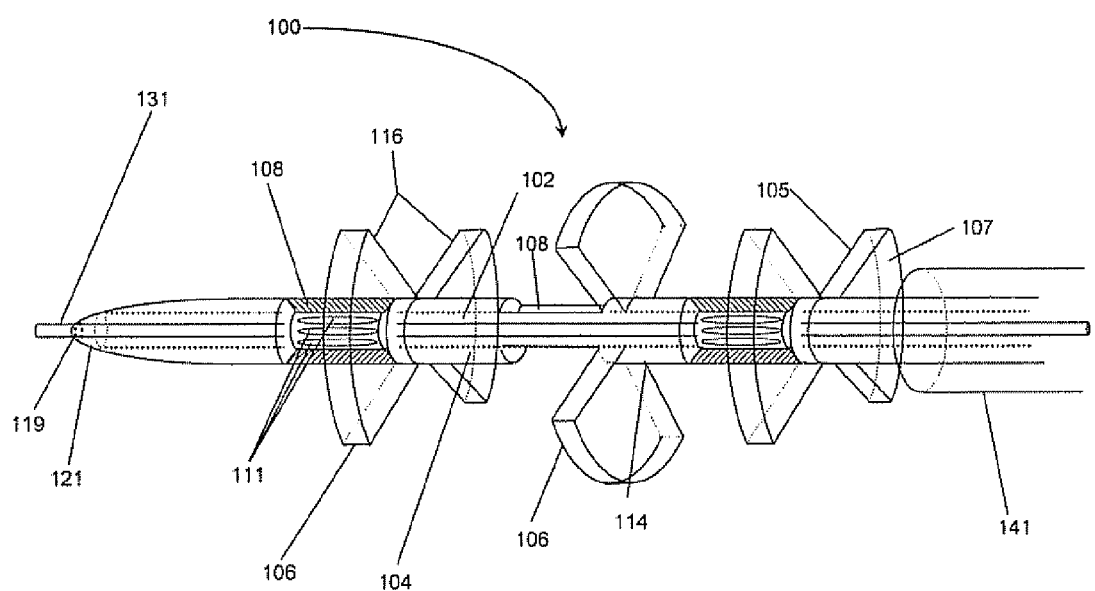
FIG. 1 is a perspective view of a catheter constructed in accordance with an embodiment of the invention.

The following discussion is directed to embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

NOTATION AND NOMENCLATURE

Certain terms are used throughout the following description and claims to refer to particular features or components. As one skilled in the art will appreciate, different persons may refer to the same feature or component by different names. This document does not intend to distinguish between components or features that differ in name but not function. The drawing figures are not necessarily to scale. Certain features and components herein may be shown exaggerated in scale or in somewhat schematic form and some details of conventional elements may not be shown in interest of clarity and conciseness.

In the following discussion and in the claims, the terms "including" and "comprising" are used in an open-ended fashion, and thus should be interpreted to mean "including, but not limited to . . . ." Also, the term "distal" is intended to refer to positions relatively away from the operator of the catheter when it is in use, while the term "proximal" is intended to refer to positions relatively near the operator when the catheter is in use. As a result, the distal end of a device is relatively near the embolus as compared to the proximal end of the device, which is relatively away from the embolus. In addition, the term "radial" is intended to refer to movement toward or away from the longitudinal central axis of the catheter. The term "axial" is meant to refer to positions lengthwise along the central axis of the catheter. The term "discrete" is intended to describe members that are individually disposed and separately inflatable. If one discrete member is obstructed and unable to fully expand, the next discrete member is not affected and may be expanded to its predetermined shape without regard to other members.

DETAILED DESCRIPTION OF EMBODIMENTS

Referring initially to FIG. 1, according to an embodiment, a catheter 100 comprises an inner lumen 102, and outer lumen 104, and a plurality of expandable members 106. Typically, catheter 100 slides coaxially over a guide wire 131. Inner lumen 102 and outer lumen 104 are sealed or separate from each other. Thus, inner and outer lumen 102, 104 are not in fluid communication with each other. Plurality of expandable members 106 are disposed axially along the shaft or body 114 of catheter 100. Moreover, outer lumen 104 is in fluid communication with plurality of expandable members 106. Any suitable number of expandable members 106 may be disposed along the body 114 of catheter 100.

In an embodiment, catheter 100 may be disposed inside a guiding catheter 141. In general, the outer diameter of guiding catheter 141 is less than the inner diameter of the occluded portion of the vessel and the outer diameter of catheter 100 is less than the inner diameter of guiding catheter 141. In other words, catheter 100 moves coaxially within lumen of guiding catheter 141.

By way of example only, in most adults, the common carotid artery has a diameter of about 6-10 mm, the internal carotid artery has a diameter of about 5-6 mm, and the middle cerebral artery has a diameter of about 2-3 mm. In certain embodiments, the guiding catheter 141 may be positioned upstream of the embolus, in the common or internal carotid artery, which has a diameter of 5-6 mm, so the guiding catheter 141 may have a diameter of 2-3 mm. In these embodiments, catheter body 114 of catheter 100 may have a diameter of 0.5 to 1 mm, so that it can enter the smaller vessel or branch where the embolus is located.

Figure 6:
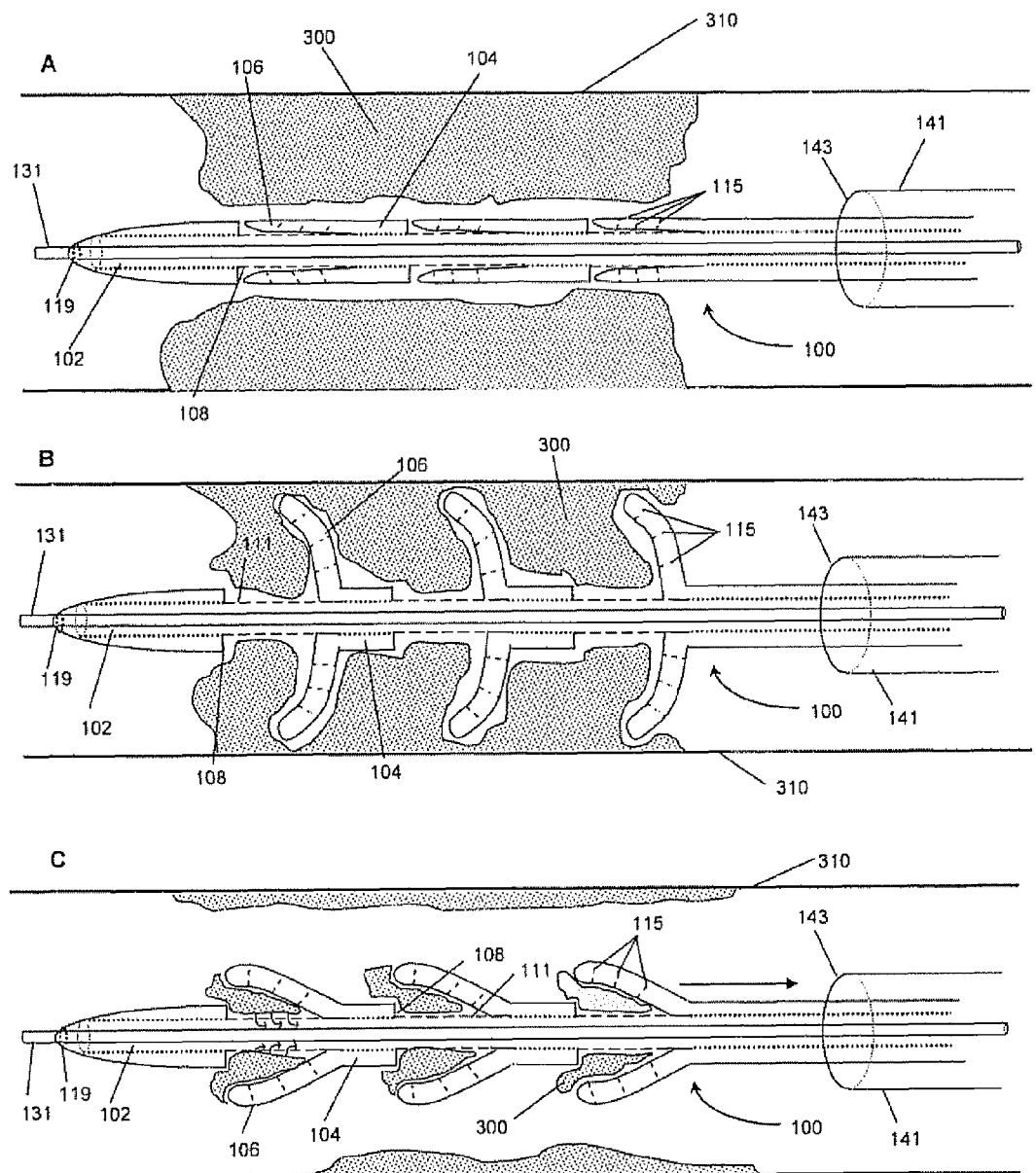
FIGS. 6A-C illustrate an embodiment of a method of removing an embolus from a vessel.

In an embodiment, plurality of expanded members 106 have an expanded position and a contracted position as seen in FIG. 6. The expanded outer diameter of each expandable member 106 in the expanded position is preferably substantially equal to or less than the inner diameter of a target vessel. The target vessel may be any blood vessel. Examples include without limitation, the carotid artery, the basilar artery, or the middle cerebral artery. In an embodiment, expanded outer diameter of each expandable member 106 will equal approximately 2.5 to 5 mm or the diameter of an average carotid artery.

Outer lumen 104 and members 106 are in fluid communication with each other and expandable members 106 are expanded by filling outer lumen 104 and members 106 with a fluid or a gas. In an embodiment, the fluid disposed in outer lumen 104 comprises a fluid, such as a radiopaque fluid. However, any suitable fluid or gas known in the art may be utilized. Members 106 expand as fluid travels through outer lumen 104 from proximal end toward distal end 121 of catheter 100.

Figure 3:
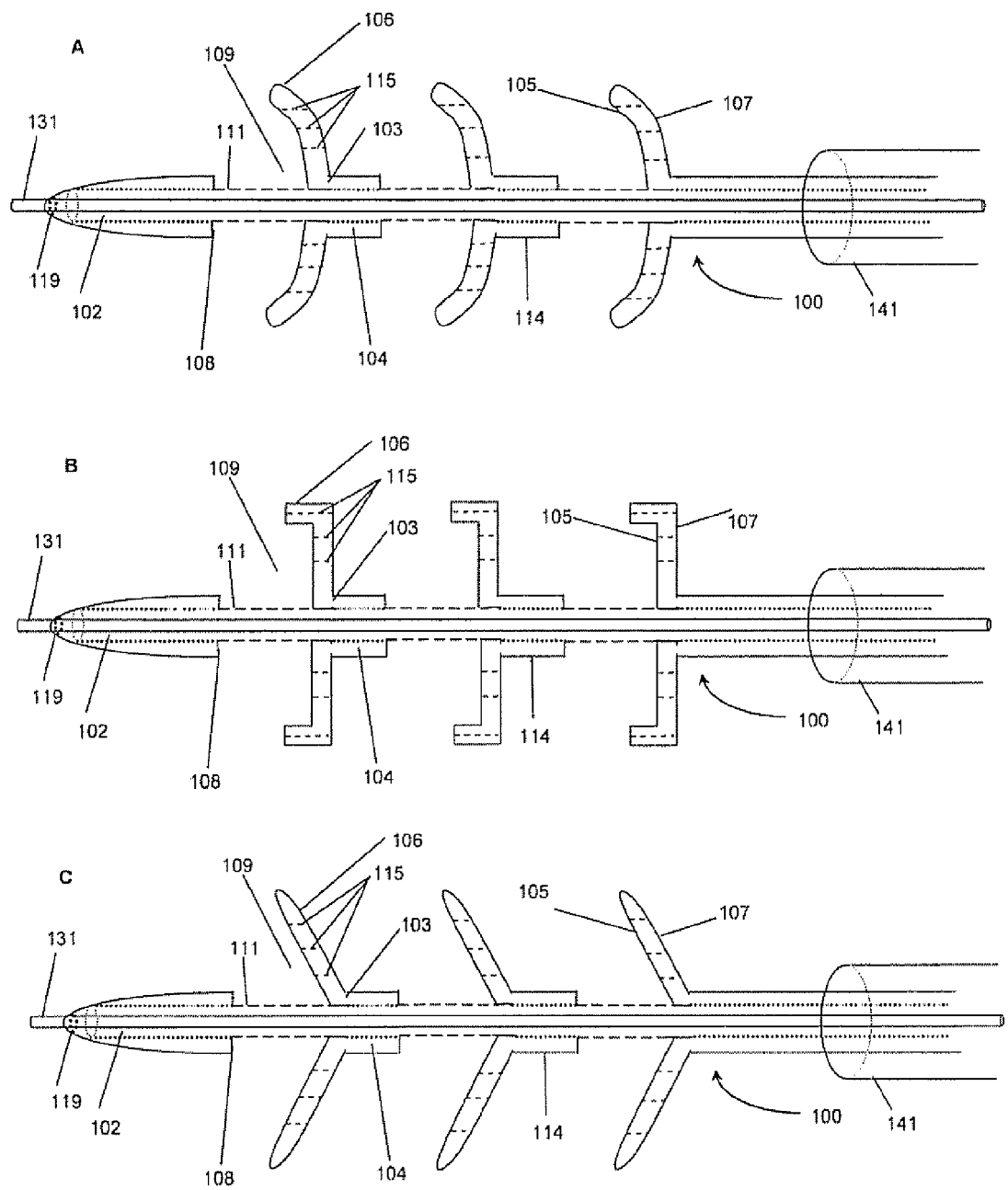
FIGS. 3A-C illustrate side views of various embodiments of a catheter with different cross-sectional configurations.

Referring to FIG. 3, in certain embodiments, fluid enters each expandable member 106 from outer lumen 104 through at least one inlet 103. According to an embodiment, the outer lumen 104 includes two inlets 103 for each member 106. Inlets are generally spaced around the circumference of catheter body 114 according to the location of each expandable member 106. Alternatively, inlets may be unevenly spaced or there may be only one inlet 103 for each expandable member 106.

Figure 5:
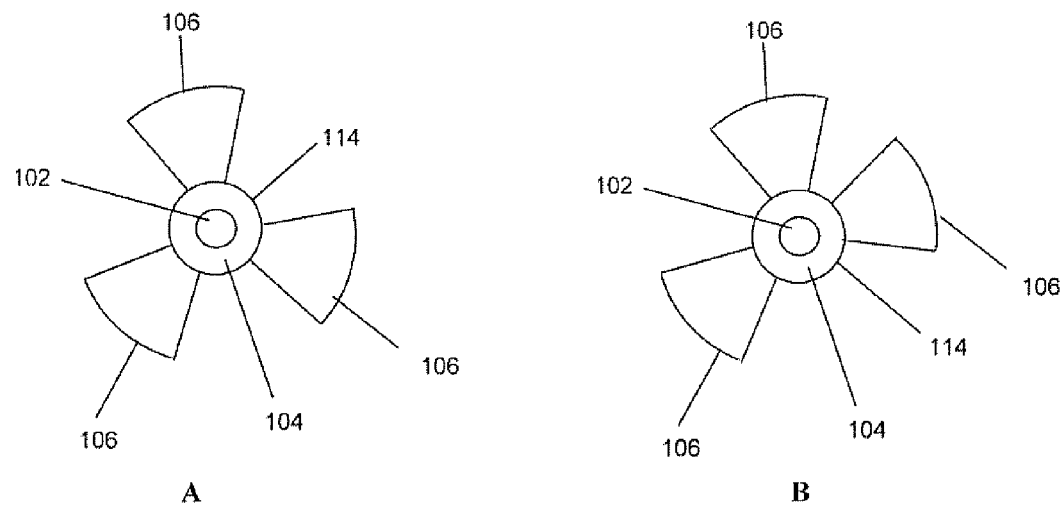
FIG. 5A is an end view down the longitudinal axis of an embodiment of a catheter comprising three expandable members per set in which the members disposed at equal angles.
FIG. 5B is an end view down the longitudinal axis of an embodiment of a catheter comprising three expandable members per set in which the members are disposed at different angles.

As illustrated in FIGS. 3A-C for example, members 106, when in their expanded position, my form a predetermined profile shape such as curved (FIG. 3A), bent (FIG. 3B), or straight (FIG. 3C). Distal surface 105 of each member 106 forms the inner surface of the cone or cup shape and proximal surface 107 forms the outer surface of the shape. In one embodiment, distal surface 105 forms an acute angle with the catheter body 114 and proximal surface 107 forms an obtuse angle with the catheter body 114 as shown in FIGS. 3A-C. However, it is to be understood that expandable members 106 may have other shapes, such as concave in the opposite direction, and/or may not all be identically sized or shaped. Furthermore, when viewed down the axial length, the expandable members 106 may comprise a variety of shapes. For instance, in FIG. 5, members 106 comprise a trapezoidal shape. In other embodiments, the members 106 may comprise a rectangular, ovoid, or any other suitable shape.

In embodiments, each expandable member 106 is preferably concave in profile. That is, when viewed in profile, each member is angled toward the distal end 121 of catheter 100 as shown for example, in FIG. 3A-C. This concavity or angling, coupled with the axial spacing of the members 106 along the catheter body 114 results in a capture space 109 that is defined between each recess 108 and each member 106. During an embolectomy, described below, portions of the embolus 300 are captured in capture space 109 between members 106 and recesses 108. As the catheter 100 is retracted, in some embodiment, distally curving outer edges on the member 106 may help retain the captured portions as seen in FIG. 3A. Alternatively, each expandable member 106 is concave in profile toward the proximal end of catheter 100 (not shown). In other words, each expandable member is concave facing away from the distal end 121 of catheter 100.

Referring now to FIG. 1, according to an embodiment, catheter 100 includes a plurality of recesses 108. Recesses 108 allow members 106 to fit flush with catheter body 114 when members 106 are in their contracted position. Thus, catheter body 114 presents a low-profile when members 106 are in their contracted position and facilitates ease of insertion into small vessels. Moreover, each recess 108 may also facilitate improved removal of emboli or clot particles by catheter 100 by entrapment of particles within recesses 108 by members 106. In embodiments, each member 106 has its own or is associated with a corresponding recess 108. Moreover, recesses 108 are arranged in the same configuration as members 106. In embodiments, recesses 108 are disposed distal to members 106. Alternatively, recesses 108 are disposed proximal to member 106.

Movement of members 106 into their contracted position or withdrawal of fluid from each member 106 reduces the overall diameter of catheter 100, so that it is less than the inner diameter of guiding catheter 102. When members 106 are in their contracted position, they preferably fit snugly within each recess 108 and cover openings 111.

In embodiments, the bottom or base of each recess 108 comprises one or more openings 111. Openings 111 allow the inner lumen 102 to be in fluid communication with the interior of the vessel. In general, openings 111 may be of any suitable geometry such as circular, rectangular, oval, etc. Additionally, openings 111 serve as a means to facilitate capture of emboli or clot particles by the application of a vacuum in inner lumen 102 through openings 111. The application of vacuum in inner lumen 102 may create suction from openings 111 to draw or pull emboli and clot particles into each recess 108. In some embodiments, openings 111 may have an area large enough entry of captured clot or tissue material. In embodiments with more than one opening 111 per recess 108, openings 111 may be arranged in any suitable configuration. For example, as shown in FIG. 1, the openings 111 may comprise parallel, elongated grooves at the bottom of each recess 108.

In an embodiment, plurality of expanded members 106 are arranged as one or more sets or arrays 116 of members 106 arranged along catheter body 114 as shown for example, in FIG. 1. In some embodiments, each set 116 contains a pair of members 106 disposed opposite each other circumferentially around catheter body 114. See FIG. 1. Additionally, in some embodiments, each set 116 of members 106 may comprise two or more members 106 disposed at any suitable angle around catheter body 114, as shown in FIGS. 5A-B. Members 106 may be disposed at equal angles (see e.g. FIG. 5A) or different angles around catheter body 114 (see e.g. FIG. 5B).

Figure 2:
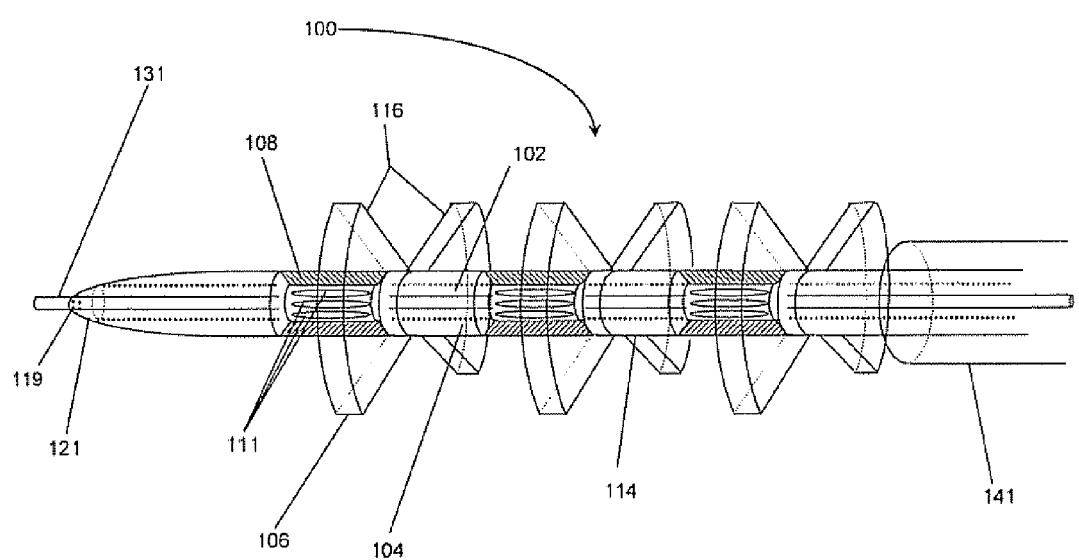
FIG. 2 illustrates an embodiment of a catheter with sets of expandable members aligned with each other.
Figure 4:
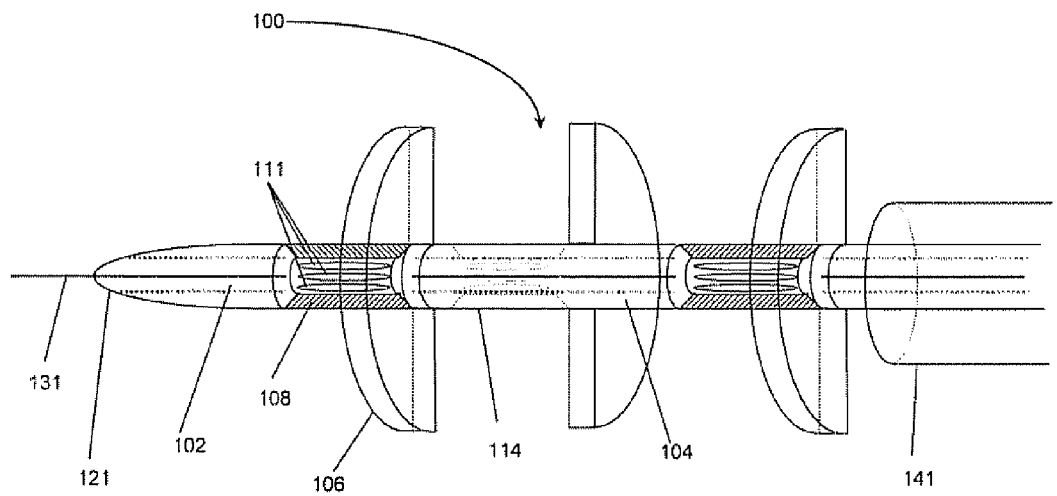
FIG. 4 illustrates an embodiment of a catheter with expandable members offset from each other.

Furthermore, catheter 100 may comprise multiple sets 116 of members 106 along catheter body 114. In embodiments, catheter 100 comprises from 1 to 8 sets of members 106. According to an embodiment, each set 116 of members 106 are offset at different angles from each other as shown in FIG. 1. In embodiments, each set 116 of members 106 is aligned at the same angles with each other as shown in FIG. 2. The offset sets or arrays 116 may facilitate more efficient trapping of emboli or clots in the vessel. In yet another embodiment, each set 116 may comprise a single member 106 where each member 106 may be offset from the others as shown in FIG. 4.

Members 106, according to one embodiment, are constructed of a resilient material that allows for expansion and contraction. In an embodiment the resilient material comprises a polymer. In other embodiments, members 106 comprise a flexible material that does not appreciably stretch. Members 106 each include a distal surface 105 aid a proximal surface 107. Members 106 are preferably spaced axially along catheter body 114 with equal distances between distal surface 105 of one member 106 and proximal surface 107 of an adjacent member 106, but may be spaced according to other configurations. In an embodiment, the distance between members 106 is in the range of about 1 mm to about 5 mm. In addition, members 106 may comprise any suitable thickness. In an embodiment, the thickness of members 106 may range from about 0.5 mm to about 4 mm.

In embodiments, catheter 100 includes a radiopaque mark (not shown) on at least the most distal segment and the most proximal segment. Such radiopaque marks aid in visualization during placement and extraction, as described below.

As shown in FIG. 3, one or more webs 115 are disposed inside members 106. The webbing serves to maintain the structural integrity of each member 106. In embodiments, webbing 115 is composed of a material that is less elastic than members 106. Webbing 115 may be disposed in one or a plurality of places inside each member 106 and shaped such that it prevents deformation of members 106 beyond their predetermined shape. In the embodiment shown, multiple webs connect each distal surface wall 105 to proximal surface 107 of the same expandable member 106, thereby limiting the ability of the member 106 to expand beyond the desired shape and more specifically limiting the ability of each member 106 to deform beyond a pre-determined expansion point between distal and proximal surfaces 105, 107.

A guide wire 131, such as is well known in the art, is typically inserted coaxially through inner lumen 102 of catheter 100. The opening at distal end of catheter 100 may comprise a seal 119. Seal 119 guides catheter 100 along guide wire 131 for proper placement within vessel 110 as described below and prevents the egress of fluid around the guide wire 131 into inner lumen 102. Seal 119 further allows vacuum to be applied within inner lumen 102 during removal of emboli or clots from the vessel.

Catheter 100, including members 106, and guide wire 131 preferably comprise materials that are biocompatible and non-thrombogenic.

Embolectomy

As illustrated in FIGS. 6A-C, catheter 100 may be disposed in an occluded branch or vessel 310 and used to remove an embolus 300 therefrom. In an embodiment, guide wire 131 is deployed in the vessel 310 through and preferably proximate to embolus 300. Catheter 100 is then deployed so that its distal end 121 penetrates the distal edge of the embolus 300 (FIG. 6A), or otherwise as desired, using guide wire 131 as a guide. As illustrated in FIG. 6A, during placement, members 106 are in their contracted position and disposed within their corresponding recesses 108 so as to maintain a low profile for the catheter 100 and facilitate insertion into small diameter vessels. Typically, fluoroscopy or an equivalent technique is used to monitor the position of catheter 100 relative to embolus 300. In particular, radiopaque marks on the expandable members 106 can help ensure that the catheter 100 is positioned as desired.

Once in the desired position, ideally with members 106 positioned within embolus 300, members 106 are expanded as fluid flows through outer lumen 104 of catheter 100. Members 106 gradually expand toward the inner wall of vessel 110, trapping portions of embolus 300 in between members 106 as seen in FIG. 6B.

In an embodiment, once members 106 have been expanded, openings 111 are exposed to vessel interior. Any type of drug or therapeutic compound may be delivered through openings 111 to the site of the clot or embolus. Thus, catheter 100 is further capable of delivering drugs to an embolus or clot in a site-specific manner. In an embodiment, the drug is capable of dissolving an embolus or clot. Examples of suitable drugs that may be used include without limitation, aspirin, thienopyridines (e.g. ticlopidine and clopidogrel), glycoprotein IIB/IIa inhibitors (e.g. abciximab and eptifibatide), tissue plasminogen activator (tPA), or combinations thereof.

In one embodiment, after members 106 are expanded to a desired state and embolus 300 is captured between members 106, a vacuum may be applied through the openings 111 located in recesses 108. See FIG. 6C. The vacuum may be applied by suction from the inner lumen 102. During application of vacuum, inflatable members 106 maintain patency of the vessel and prevent collapse of the vessel wall due to suction from recesses 108. In an exemplary embodiment, a vacuum line (not shown) may be attached to proximal end of catheter 100 to apply vacuum. However, it is contemplated that other methods known to those in the art for applying vacuum through a catheter may be used.

Vacuum applied through openings 111 may serve several purposes. For example, vacuum may allow for more efficient trapping of embolus particles caught between members 106 into each recess 108. In some embodiments, openings 111 are large enough to allow passage of trapped clot or embolus particles into the inner lumen 102 for even more effective removal of the embolus or clot. Thus, portions of the embolus or clot may be sucked into the inner lumen 102 via openings 111 and removed.

Once it is determined that the embolus 300 is securely trapped either through suction or the action of members 106, catheter 100 is drawn toward guiding catheter 141. In an embodiment, as members 106 approach distal opening 143 of guiding catheter 141, fluid is gradually released from the outer lumen 104 of catheter 100 such that members 106 are contracted sequentially so as to maintain the trapping effect on a portion of the embolus 300 while allowing members 106 to fit within guiding catheter 102 and reducing the overall volume of member 106, so as to allow capture of a maximum portion of the embolus 300. In an embodiment, it is envisioned that the contracting of members 106 is due to the combined effect of fluid withdrawal from members 106, application of vacuum from openings 111, and withdrawals of catheter 100 into guiding catheter 141. However, in other embodiments, the contracting of members 106 may be accomplished by each of the aforementioned mechanisms individually.

In some instances, collection of the embolus 300 can be facilitated by applying suction to inside of guiding catheter 141. That is, a vacuum may be further applied to guiding catheter to pull emboli particle captured by member 106 into guiding catheter, thus, enhancing removal of the embolus 300 from vessel 310.

Preferably after distal end 121 is drawn into guiding catheter 141, catheter 100 is withdrawn proximally from the occluded region, removing at least a portion of the embolus.

If embolus 300 is larger than can be removed by members 106 with one procedure, then the procedure may be repeated to remove the occlusion. It is envisioned that the methods and devices described herein will not be limited to emboli and clots, but also for removing any obstruction deposited in blood vessels such as atherosclerotic plaque.

While embodiments of the invention are shown and described, it will be understood that variations to these embodiments can be made without departing from the scope of the invention. Likewise, the sequential description or claiming of certain steps of disclosed methods are not intended to limit the methods to performance of those steps in that order or in any particular order, unless otherwise stated.

What is claimed is:

1. A catheter comprising:
   a) a catheter body having an inner lumen, an outer lumen, and a plurality of recesses disposed along said catheter body, wherein each recess includes at least one opening configured to be in fluid communication between said inner lumen and a vessel, and wherein said inner lumen and outer lumen are sealed from each other; and
   b) a plurality of expandable members disposed along said catheter body in fluid communication with said outer lumen, wherein each expandable member has an expanded position and a contracted position, and wherein each expandable member in said contracted position fits within one of said plurality of recesses and can entrap emboli.

2. The catheter of claim 1 wherein said plurality of expandable members are disposed along said catheter body as sets of expandable members, wherein each set comprises at least one expandable member.

3. The catheter of claim 2 wherein each set comprises at least two expandable members.

4. The catheter of claim 2 wherein each expandable member in each set is disposed circumferentially around said catheter body.

5. The catheter of claim 2 wherein each set of expandable members is aligned with each other.

6. The catheter of claim 2 wherein each set of expandable members is offset from each other.

7. The catheter of claim 2 wherein each set of expandable member comprises different numbers of expandable members.

8. The catheter of claim 1 wherein said one or more openings are elongated.

9. The catheter of claim 1, further comprising a guide wire disposed coaxially within said inner lumen.

10. The catheter of claim 9, further including a seal at a distal end of said catheter, wherein said guide wire extends through said seal.

11. The catheter of claim 1 wherein said expandable members comprise a resilient material.

12. The catheter of claim 1 wherein said plurality of expandable members are radially expandable.

13. The catheter of claim 1 wherein each expandable member has a concave profile in said expanded position.

14. The catheter of claim 1 wherein each expandable member is angled distally in said expanded position.

15. The catheter of claim 1 wherein a plurality of recesses have the same diameters of said plurality of expandable members.

16. The catheter of claim 1 wherein a web is affixed inside each of said plurality of expandable members.

17. The catheter of claim 16 wherein said web comprises a less resilient material than that of said plurality of expandable members.

18. The device of claim 12 further comprising a guide wire slidably disposed within the inner lumen of said catheter.

19. The catheter of claim 1 wherein said plurality of expandable members are disposed along said catheter body as sets of expandable members, wherein expansion and contraction of the expandable members captures a portion of the embolus within the recesses.

20. The catheter of claim 1 further comprising an opening within each recess fluid communicable through an inner lumen with a suction device.

21. The catheter of claim 1 further comprising expandable members that can be separately expanded and contracted.

22. The catheter of claim 1 further comprising a plurality of expandable members separated by non expanding lumen segments.

23. The catheter of claim 1 further comprising suction within the inner lumen during removal of emboli from the vessel.

24. The catheter of claim 1 wherein the expansion and contraction of expandable members captures a portion of the embolus.

25. The catheter of claim 1 further comprising a guiding catheter.

26. The guiding catheter of claim 25 further comprising suction.

\* \* \* \* \*

UNITED STATES PATENT AND TRADEMARK OFFICE
CERTIFICATE OF CORRECTION

| | | |
|---|---|---|
| PATENT NO. | : 7,914,549 B2 | Page 1 of 1 |
| APPLICATION NO. | : 11/620387 | |
| DATED | : March 29, 2011 | |
| INVENTOR(S) | : Hesham Morsi | |

It is certified that error appears in the above-identified patent and that said Letters Patent is hereby corrected as shown below:

Col. 2, line 20 replace "this" with "those"
Col. 5, line 5 replace "my" with "may"

Signed and Sealed this
Tenth Day of May, 2011

David J. Kappos
*Director of the United States Patent and Trademark Office*